United States Patent
Lim et al.

(10) Patent No.: US 11,970,443 B2
(45) Date of Patent: Apr. 30, 2024

(54) CROSSLINKING AGENT COMPOUND AND SUPERABSORBENT POLYMER PREPARED BY USING THE SAME

(71) Applicant: LG Chem, Ltd., Seoul (KR)

(72) Inventors: Won Taeck Lim, Daejeon (KR); Wonmun Choi, Daejeon (KR); Gicheul Kim, Daejeon (KR); Ki Hyun Kim, Daejeon (KR); Seul Ah Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 938 days.

(21) Appl. No.: 16/966,324

(22) PCT Filed: Oct. 18, 2019

(86) PCT No.: PCT/KR2019/013767
§ 371 (c)(1),
(2) Date: Jul. 30, 2020

(87) PCT Pub. No.: WO2020/080894
PCT Pub. Date: Apr. 23, 2020

(65) Prior Publication Data
US 2020/0369595 A1    Nov. 26, 2020

(30) Foreign Application Priority Data

Oct. 18, 2018  (KR) .................. 10-2018-0124565
Oct. 17, 2019  (KR) .................. 10-2019-0129388

(51) Int. Cl.
| | | |
|---|---|---|
| C07C 69/606 | (2006.01) | |
| B01J 20/26  | (2006.01) | |
| C08F 20/06  | (2006.01) | |
| C08J 3/24   | (2006.01) | |

(52) U.S. Cl.
CPC ........... *C07C 69/606* (2013.01); *B01J 20/267* (2013.01); *C08F 20/06* (2013.01); *B01J 2220/68* (2013.01); *C08J 3/245* (2013.01)

(58) Field of Classification Search
CPC ... C07C 69/606; B01J 20/267; B01J 2220/68; C08F 20/06; C08J 3/245
USPC ....................................................... 528/303
See application file for complete search history.

(56) References Cited

U.S. PATENT DOCUMENTS

| | | |
|---|---|---|
| 7,601,482 B2      | 10/2009 | Pawlowski et al. |
| 2006/0247377 A1   | 11/2006 | Riegel et al. |
| 2008/0140037 A1   | 6/2008  | Newman |
| 2014/0377668 A1 * | 12/2014 | Abe ............... H01M 10/0569 429/188 |
| 2020/0392065 A1   | 12/2020 | Kakuta et al. |

FOREIGN PATENT DOCUMENTS

| | | | |
|---|---|---|---|
| JP | 2008522003 A  |   | 6/2008  |
| JP | 2010093065 A  | * | 4/2010  |
| JP | 2010093065 A  |   | 4/2010  |
| JP | 6024670 B2    |   | 11/2016 |
| KR | 20140116154 A |   | 10/2014 |
| KR | 20180075313 A |   | 7/2018  |
| WO | 2019171957 A1 |   | 9/2019  |

OTHER PUBLICATIONS

Clavier et al, Chemodivergent Metathesis of Dienynes Catalyzed by Ruthenium-Indenylidene Complexes: An Experimental and Computational Study, Chem. Eur. J., Oct. 5, 2009, pp. 10244-10254, vol. 15, No. 39.
International Search Report for Application No. PCT/KR2019/013767 dated Feb. 6, 2020, 2 pages.
Van Boxtel et al, Facile Synthesis of Bicyclic and Tricyclic Skeletons by Cycloisomerizations of Hept-1-en-6-ynes and 4,9-Diheteradodeca-1,11-dien-6cynes, Followed by [4+2] Cycloadditions, Eur. J. Org. Chem., Jun. 2001, pp. 2283-2292, vol. 12.
Extended European Search Report including Written Opinion for Application No. 19874630.7 dated Mar. 19, 2021, pp. 1-8.
Nakatake, Daiki et al., "Chemoselective Transesterification of Acrylate Derivatives for Functionalized Monomer Synthesis using a Hard Zinc Alkoxide Generation Strategy", European Journal of Organic Chemistry, Aug. 2016, pp. 3696-3699, vol. 2016, No. 22, WILEY-VCH, Weinheim.

* cited by examiner

*Primary Examiner* — Ling Siu Cho
*Assistant Examiner* — Ronald Grinsted
(74) *Attorney, Agent, or Firm* — Lerner David LLP

(57) ABSTRACT

Provided are a novel crosslinking agent compound, and a superabsorbent polymer prepared by using the same. More particularly, provided are a crosslinking agent compound having a novel structure, which exhibits excellent crosslinking property and thermal degradability, and a superabsorbent polymer prepared by using the same.

13 Claims, No Drawings

CROSSLINKING AGENT COMPOUND AND SUPERABSORBENT POLYMER PREPARED BY USING THE SAME

CROSS-REFERENCE TO RELATED APPLICATION

The present application is a national phase entry under 35 U.S.C. § 371 of International Application No. PCT/KR2019/013767, filed Oct. 18, 2019, which claims priority to Korean Patent Application Nos. 10-2018-0124565 and 10-2019-0129388, filed eft Oct. 18, 2018 and Oct. 17, 2019, the disclosures of which are incorporated herein by reference.

TECHNICAL FIELD

The present invention relates to a novel crosslinking agent compound and a superabsorbent polymer prepared by using the same. More particularly, the present invention relates to a crosslinking agent compound having a novel structure, which exhibits excellent crosslinking property and thermal degradability, and a superabsorbent polymer prepared by using the same.

BACKGROUND ART

A superabsorbent polymer (SAP) is a synthetic polymeric material capable of absorbing moisture from 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, sanitary pads, etc., but also for water retaining soil products for gardening, water stop materials for the civil engineering and construction, sheets for raising seedling, fresh-keeping agents for food distribution fields, materials for poultice or the like.

In most cases, these superabsorbent polymers have been widely used in the field of hygienic materials such as diapers, sanitary pads, etc. For these applications, superabsorbent polymers are required to exhibit high absorbency with respect to water, etc., not to release the absorbed water even under an external pressure, and also to well maintain their shape even in a state where the volume is expanded (swelled) by absorbing water, thereby exhibiting excellent liquid permeability.

Therefore, in order for the superabsorbent polymer to have excellent performance, the base resin which is the most important component is required to have high absorbency.

To prepare such a base resin, crosslinking density inside the polymer may be generally controlled by polymerizing an acrylic acid-based monomer in the presence of an internal crosslinking agent. The internal crosslinking agent is to crosslink the inside of the polymer obtained by polymerizing the acrylic acid-based monomer, i.e., the base resin. The internal crosslinking density of the base resin may be controlled according to the type and content of the internal crosslinking agent. If the crosslinking density of the base resin is low, the absorbency becomes high, but the strength becomes weak, which may cause a problem that its shape is not maintained in a subsequent process. If the crosslinking density is too high, the strength becomes high, but the water absorbency may be decreased. Thus, it is very important to control the appropriate crosslinking density in terms of strength and absorbency of the base resin.

For the above-described reasons, there is a limitation in providing a superabsorbent polymer having improved water retention capacity and absorbency under pressure at the same time. In order to solve this problem, various attempts have been made to improve these physical properties by controlling the type or amount of the internal crosslinking agent or surface crosslinking agent, but these attempts have been limited.

DISCLOSURE

Technical Problem

To solve the above problem, the present invention provides a crosslinking agent compound having a novel structure, which has excellent crosslinking property, thermal degradability, reactivity, etc., thereby being used as a crosslinking agent during preparation of a superabsorbent polymer, and a superabsorbent polymer prepared by using the same.

Technical Solution

To solve the above problem, one embodiment of the present invention provides a crosslinking agent compound represented by the following Chemical Formula 1:

[Chemical Formula 1]

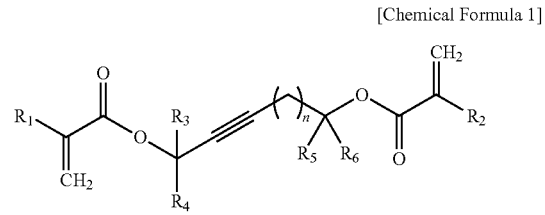

in Chemical Formula 1, $R_1$ and $R_2$ are each independently hydrogen or methyl, $R_3$ to $R_6$ are each independently hydrogen, alkyl having 1 to 20 carbon atoms, or cycloalkyl having 3 to 20 carbon atoms, wherein among $R_3$ to $R_6$, two or more adjacent to each other may be connected to each other to form a divalent aliphatic ring, and n is an integer of 0 to 10.

Further, another embodiment of the present invention provides a superabsorbent polymer including a polymer which is obtained by polymerizing the crosslinking agent compound and an acrylic acid-based monomer.

Effect of the Invention

A crosslinking agent compound of the present invention is a compound having a novel structure, which has not been known in the art, and includes a carbon-carbon triple bond. A polymer obtained by polymerizing the crosslinking agent compound of the present invention and an acrylic acid-based monomer may exhibit thermal degradability in which a crosslinked structure is degraded at a predetermined temperature or higher.

Therefore, the polymer obtained by using the crosslinking agent compound of the present invention exhibits high crosslinking density immediately after polymerization, thereby exhibiting high strength and excellent processibility. However, the internal crosslinked structure is degraded in a subsequent high-temperature process, and thus the crosslinking density is decreased, thereby improving absorbency.

DETAILED DESCRIPTION OF THE EMBODIMENTS

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, a crosslinking agent compound of the present invention and a superabsorbent polymer prepared by using the same will be described in more detail.

Crosslinking Agent Compound

A crosslinking agent compound according to one embodiment of the present invention is represented by the following Chemical Formula 1:

[Chemical Formula 1]

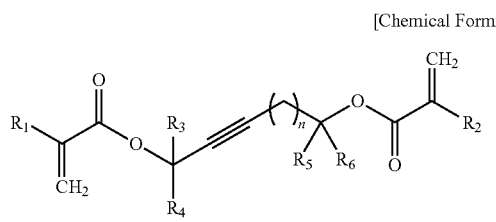

in Chemical Formula 1, $R_1$ and $R_2$ are each independently hydrogen or methyl, $R_3$ to $R_6$ are each independently hydrogen, alkyl having 1 to 20 carbon atoms, or cycloalkyl having 3 to 20 carbon atoms, wherein among $R_3$ to $R_6$, two or more adjacent to each other may be connected to each other to form a divalent aliphatic ring, and n is an integer of 0 to 10.

As used herein, "alkyl" refers to a linear or branched, saturated monovalent hydrocarbon having 1 to 20 carbon atoms, preferably 1 to 10 carbon atoms, and more preferably 1 to 5 carbon atoms. Examples of the alkyl may include methyl, ethyl, propyl, n-propyl, isopropyl, n-butyl, isobutyl, tert-butyl, sec-butyl, 1-methyl-butyl, 1-ethyl-butyl, n-pentyl, isopentyl, neopentyl, tert-pentyl, n-hexyl, isohexyl, 1-methylpentyl, 2-methylpentyl, 4-methyl-2-pentyl, 3,3-dimethylbutyl, 2-ethylbutyl, n-heptyl, 1-methyihexyl, n-octyl, tert-octyl, 1-methyiheptyl, 2-ethylhexyl, 2-propylpentyl, n-nonyl, 2,2-dimethylheptyl, 1-ethyl-propyl, 1,1-dimethylpropyl, 2-methylpentyl, 4-methyihexyl, 5-methyihexyl, etc., but the present invention is not limited thereto.

Further, "cycloalkyl" "alkyl" refers to a saturated aliphatic monovalent cyclic hydrocarbon having 3 to 20 carbon atoms, preferably 4 to 10 carbon atoms, and more preferably 5 to 10 carbon atoms. Examples of the cycloalkyl may include cyclopropyl, cyclobutyl, cyclopentyl, cyclohexyl, etc., but the present invention is not limited thereto.

The crosslinking agent compound of Chemical Formula 1, which is a di(meth)acrylate-based derivative compound including a carbon-carbon triple bond, has a novel structure.

According to one exemplary embodiment of the present invention, $R_1$ and $R_2$ may be hydrogen.

According to one exemplary embodiment of the present invention, $R_3$ to $R_6$ may be each independently hydrogen or alkyl having 1 to 5 carbon atoms. Preferably, $R_3$ to $R_6$ may be hydrogen, methyl, or ethyl. Alternatively, $R_3$ to $R_6$ may be a divalent form of cycloalkane formed by connecting two groups adjacent to each other.

According to one exemplary embodiment of the present invention, n may be an integer of 0 to 5, or 0 to 3, or 0 to 1.

According to one exemplary embodiment of the present invention, the compound represented by Chemical Formula 1 may be any one selected from the group consisting of the following Chemical Formulae 1-1 to 1-3, but the present invention is not limited thereto.

[Chemical Formula 1-1]

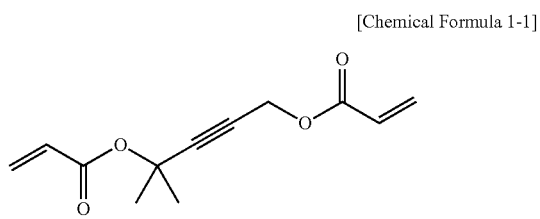

[Chemical Formula 1-2]

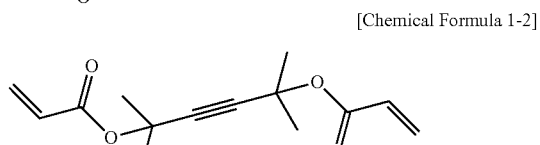

[Chemical Formula 1-3]

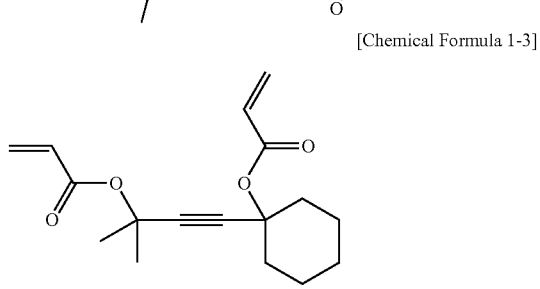

The compound represented by Chemical Formula 1 may be, but is not limited to, used as a crosslinking agent when polymerized with an acrylic acid-based monomer during preparation of a superabsorbent polymer.

In order for the superabsorbent polymer to exhibit excellent physical property in terms of absorbency, a crosslinked polymer of an acrylic acid-based monomer, i.e., a base resin is basically required to exhibit high absorbency, and to this end, it is necessary to increase the area of pores by lowering the internal crosslinking density of the base resin. In this case, however, due to the instability of the internal structure, it is difficult to maintain the shape of the base resin, which causes non-uniformity in performance due to non-uniformity of the base resin during subsequent processing such as pulverizing, drying, surface crosslinking, etc. Such non-uniformity adversely affects maintenance of product quality. In order to solve this problem, various attempts have been made to improve the physical properties by controlling the type or amount of the internal crosslinking agent, but there are various limitations in reducing the crosslinking density by controlling the amount of the internal crosslinking agent.

Accordingly, the present invention has found that this problem may be solved by providing a novel thermally degradable internal crosslinking agent which is degraded at a specific temperature.

When a crosslinked polymer is prepared by crosslinking polymerization of the acrylic acid-based monomer in the presence of the thermally degradable internal crosslinking agent compound of the present invention, thermal degradation of the thermally degradable internal crosslinking agent occurs at a specific temperature, and thus the internal crosslinking density is reduced, and as a result, absorbency of the superabsorbent polymer is increased. Meanwhile, the thermally degradable internal crosslinking agent compound of the present invention includes a carbon-carbon triple bond (alkynyl). This carbon-carbon triple bond is maintained as it is in the structure of the crosslinked polymer, thereby contributing to maintenance of the shape of the base resin, independent of the increase of absorbency. Further, even after performing a surface crosslinking reaction of the base resin, both of water retention capacity and absorbency under pressure may be maintained at a high level.

The crosslinking agent compound of Chemical Formula 1 may be prepared according to a known organic synthesis method, and for example, may be prepared by a method as in the following Reaction Scheme 1, but the present invention is not limited thereto.

[Reaction Scheme 1]

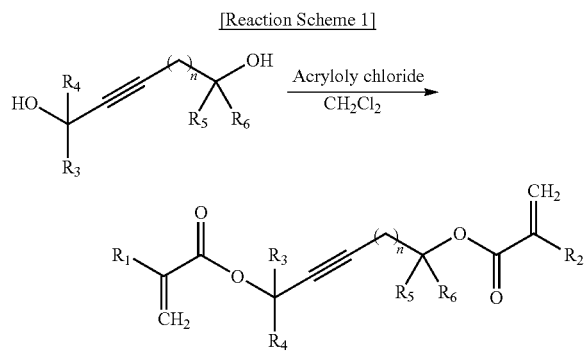

in Reaction Scheme 1, $R_1$ to $R_6$, and n are the same as defined in Chemical Formula 1.

Another embodiment of the present invention provides a superabsorbent polymer including a crosslinked polymer which is obtained by crosslinking polymerization of the acrylic acid-based monomer and the crosslinking agent compound represented by Chemical Formula 1.

The acrylic acid-based monomer is a compound represented by the following Chemical Formula 2:

 R—COOM         [Chemical Formula 2]

in Chemical Formula 2,

R is an alkyl group containing an unsaturated bond and having 2 to 5 carbon atoms, and M is a hydrogen atom, a monovalent or divalent metal, an ammonium group, or an organic amine salt.

Preferably, the acrylic acid-based monomer may include one or more selected from the group consisting of acrylic acid, methacrylic acid, and a monovalent metal salt thereof, a divalent metal salt thereof, an ammonium salt thereof, and an organic amine salt thereof.

Here, the acrylic acid-based monomer may have acidic groups, of which at least a part is neutralized.

For reference, as used herein, the "polymer" or "crosslinked polymer" means a polymerized state of the acrylic acid-based monomer in the presence of the crosslinking agent compound of Chemical Formula 1, and may encompass polymers in all ranges of water content or particle size. Among the polymers, a polymer having a water content of about 40% by weight or more after polymerization and before drying may be referred to as a water-containing gel polymer.

Further, a "base resin" or "base resin powder", which is a powder prepared by drying and pulverizing the polymer, refers to a polymer before performing the surface-crosslinking step, in which a crosslinked structure is not formed on the surface of the polymer.

The crosslinking agent compound represented by Chemical Formula 1 is a thermally degradable internal crosslinking agent, and the internal crosslinked structure of the polymer which is prepared by crosslinking polymerization of the compound of Chemical Formula 1 and the acrylic acid-based monomer may be degraded by heat (e.g., 180° C. or higher). Therefore, crosslinking polymerization of the acrylic acid-based monomer is performed in the presence of the crosslinking agent compound of Chemical Formula 1, thereby providing a crosslinked polymer into which a thermally degradable internal crosslinked structure is introduced.

Thereafter, when such a crosslinked polymer is introduced into a high-temperature subsequent process such as a surface crosslinking process, the crosslinked structure derived from the compound of Chemical Formula 1 inside the crosslinked polymer is at least partially degraded. As a result, the internal crosslinking density in the crosslinked polymer may be decreased. In contrast, the surface of the crosslinked polymer is further crosslinked by a surface crosslinking agent, and as a result, external crosslinking density is increased. Accordingly, crosslinking polymerization of the acrylic acid monomer is performed in the presence of the crosslinking agent compound represented by Chemical Formula 1 to prepare the base resin, this base resin is subjected to a subsequent process such as surface crosslinking, the internal crosslinked structure in the crosslinked polymer is degraded, and the surface of the crosslinked polymer is further crosslinked, thereby obtaining a superabsorbent polymer in which the crosslinking density increases from inside to outside of the polymer.

The superabsorbent polymer thus prepared may have reduced internal crosslinking density, as compared with the base resin of the existing superabsorbent polymer. Therefore, the superabsorbent polymer may exhibit relatively improved water retention capacity, as compared with the existing superabsorbent polymer.

Further, the superabsorbent polymer may have a surface crosslinked layer thicker than the existing superabsorbent polymer by progression of surface crosslinking after or while the internal crosslinked bond is degraded. As a result, the superabsorbent polymer may exhibit excellent absorbency under pressure. Accordingly, as the crosslinking density increases from inside to outside of the superabsorbent polymer of one embodiment, the superabsorbent polymer may exhibit excellent characteristics by improving all physical properties such as water retention capacity and absorbency under pressure, unlike traditional common knowledge that water retention capacity and absorbency under pressure are inversely related to each other.

Meanwhile, when a traditional diacrylate-based compound containing no carbon-carbon triple bond is used as an internal crosslinking agent, the water retention capacity of the superabsorbent polymer may be improved, but the absorbency under pressure may be lowered, indicating that the physical properties are not suitable for application to a final product. This phenomenon appears to be caused by the loosening of the structure due to the increased space after thermal degradation. In contrast, the crosslinking agent compound of the present invention may have the effects of improving the water retention capacity while maintaining the absorbency under pressure of the superabsorbent polymer due to the rigid structure of the carbon-carbon triple bond.

Accordingly, the polymer obtained by crosslinking polymerization of the acrylic acid-based monomer and the crosslinking agent compound represented by Chemical Formula 1 according to one embodiment of the present invention may have 5% or more, for example, 5% to 30%, or 5% to 25% increased centrifuge retention capacity (CRC) after exposure to a temperature of 180° C. or higher, for example, a temperature of 185° C. for 40 minutes before surface crosslinking, as compared with that before exposure.

Further, the polymer may be further crosslinked with a known internal crosslinking agent, in addition to the crosslinking agent compound of Chemical Formula 1.

As the known internal crosslinking agent, a compound containing two or more crosslinkable functional groups in the molecule may be used. Specific examples of the known internal crosslinking agent may include one or more selected from the group consisting of N,N'-methylene bisacrylamide, trimethylolpropane tri(meth)acrylate, ethylene glycol di(meth)acrylate, polyethylene glycol(meth)acrylate, propylene glycol di(meth)acrylate, polypropylene glycol(meth)acrylate, butanedioldi(meth)acrylate, butylene glycoldi(meth)acrylate, diethylene glycol di(meth)acrylate, hexanedioldi(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, ethylene glycol diglycidyl ether, propylene glycol, glycerin, and ethylene carbonate, but the present invention is not limited thereto.

The superabsorbent polymer of the present invention may further include a surface-crosslinked layer which is formed on the surface of the polymer.

The surface crosslinking may be performed by a common method of increasing crosslinking density of the surface of the polymer particle, and for example, a solution including the surface crosslinking agent is mixed with the polymer to allow crosslinking reaction. Further, as long as the surface crosslinking agent is a compound that is reactive with the functional group of the polymer, it may be used without limitation in the constitution thereof.

The superabsorbent polymer including the polymer and the surface-crosslinked layer formed on the surface of the polymer according to one embodiment of the present invention may have centrifuge retention capacity (CRC) of 33 g/g or more, or 34 g/g or more and 50 g/g or less, or 45 g/g or less, as measured in accordance with EDANA NWSP 241.0.R2.

Further, the superabsorbent polymer including the polymer and the surface-crosslinked layer formed on the surface of the polymer according to one embodiment of the present invention may have absorbency under pressure (AUP) of 0.7 psi of 21 g/g or more, or 22 g/g or more and 30 g/g or less, or 28 g/g or less, as measured in accordance with EDANA NWSP 242.0.R2.

As described above, the polymer of the present invention may have very excellent characteristics of both improved water retention capacity and absorbency under pressure, because partial degradation of the thermally degradable internal crosslinked structure occurs in the high-temperature subsequence process after the polymerization process, due to the characteristic of the novel crosslinking agent compound of Chemical Formula 1, and thus the crosslinking density increases from inside to outside.

Accordingly, the superabsorbent polymer may provide sanitary products, such as diapers, etc., which exhibit excellent absorption properties, even though it undergoes the high-temperature production process.

Hereinafter, the actions and effects of the present invention will be described in more detail with reference to the specific Examples of the present invention. However, these Examples are for illustrative purposes only, and the scope of the present invention is not intended to be limited thereby.

EXAMPLE

Synthesis Example of Crosslinking Agent Compound

Example 1

Synthesis of 4-methylpent-2-yne-1,4-diyl diacrylate (1) Synthesis of Diol Compound

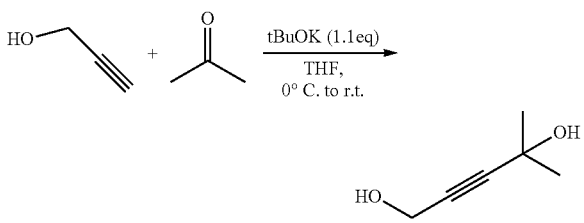

123.4 g (1.1 equivalents) of tBuOK (potassium tert-butoxide) was dissolved in THF, and then cooled to 0° C. under stirring. To this reaction solution, 56.1 g of propargyl alcohol (reference material, 1 equivalent) dissolved in THF was slowly added dropwise with paying attention to temperature rise. After stirring for about 30 minutes, 81.5 g of acetone (1.1 equivalents) was slowly added dropwise to the reaction solution. After completion of the injection, stirring was performed for about 12 hours while raising the reaction temperature to room temperature. After TLC was used to determine the completion of the reaction, the reaction mixture was decompressed to remove THF and unreacted acetone. Water and hexane were added to the remaining organic oil to remove nonpolar side reaction products with a hexane layer.

An aqueous layer was saturated by adding salt thereto, and extracted three to four times using EA. The resulting 4-methylpent-2-yne-1,4-diol was extracted as an organic layer, and the remaining water in the organic layer was removed with Na$_2$SO$_4$.

A solid phase was removed using a filter and the remaining organic solvent was removed under vacuum to obtain a desired 4-methylpent-2-yne-1,4-diol in a yield of about 95%.

(2) Synthesis of Crosslinking Agent Compound

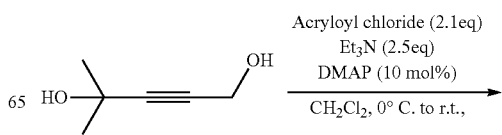

-continued

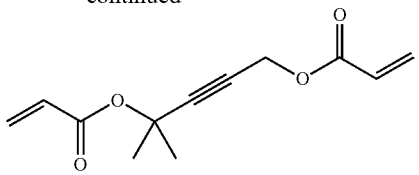

5.7 g of 4-methylpent-2-yne-1,4-diol synthesized in (1) was dissolved in 50 ml (1.0 M) of CH$_2$Cl$_2$ and the temperature was decreased to 0° C. while stirring. 12.6 g (2.5 equivalents) of triethylamine and 610 mg (0.1 equivalent) of DMAP were added, and then 9.5 g (2.1 equivalents) of acryloyl chloride was slowly added.

After completion of the addition, the reaction temperature was raised to room temperature and stirring was performed for about 12 hours. After completion of the reaction, the reaction solvent was filtered through a celite pad and the solvent was removed under vacuum. The remaining organic products were extracted with water and EA, and the remaining water in the organic layer was removed with Na$_2$SO$_4$. The solid phase was filtered off, and the remaining organic solvent was removed under vacuum to obtain the title crosslinking agent compound in a yield of 77%.

1H NMR (500 MHz, CDCl3): δ 6.45 (dd, J=17.4, 1.2 Hz, 1H), 6.37 (dd, J=17.4, 1.2 Hz, 1H), 6.15 (dd, J=17.4, 10.5 Hz, 1H), 6.06 (dd, J=17.5, 10.5 Hz, 1H), 5.87 (dd, J=10.5, 1.2 Hz, 1H), 5.80 (dd, J=10.5, 1.2 Hz, 1H), 4.81, (s, 2H), 1.71 (s, 6H)

Example 2

Synthesis of 2,5-dimethylhex-3-yne-2,5-diyl diacrylate (1) Synthesis of Diol Compound

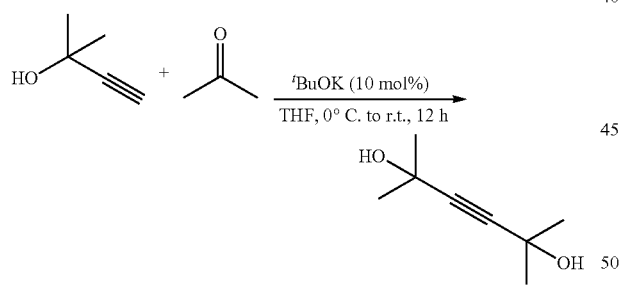

1.12 g (0.1 equivalent) of tBuOK (potassium tert-butoxide) was dissolved in THF, and then cooled to 0° C. under stirring. To this reaction solution, 8.4 g of 2-methylbut-3-yn-2-ol (reference material, 1 equivalent) dissolved in THF was slowly added dropwise with paying attention to temperature rise. After stirring for about 30 minutes, 5.8 g (1.1 equivalents) of acetone was slowly added dropwise to the reaction solution. After completion of the injection, stirring was performed for about 12 hours while raising the reaction temperature to room temperature. After TLC was used to determine the completion of the reaction, the reaction mixture was decompressed to remove THF and unreacted acetone. Water and hexane were added to the remaining organic oil to remove nonpolar side reaction products with a hexane layer.

An aqueous layer was saturated by adding salt thereto, and extracted three to four times using EA. The resulting 2,5-dimethylhex-3-yne-2,5-diol was extracted as an organic layer, and the remaining water in the organic layer was removed with Na$_2$SO$_4$. A solid phase was removed using a filter and the remaining organic solvent was removed under vacuum to obtain a desired 2,5-dimethylhex-3-yne-2,5-diol in a yield of about 95%.

(2) Synthesis of Crosslinking Agent Compound

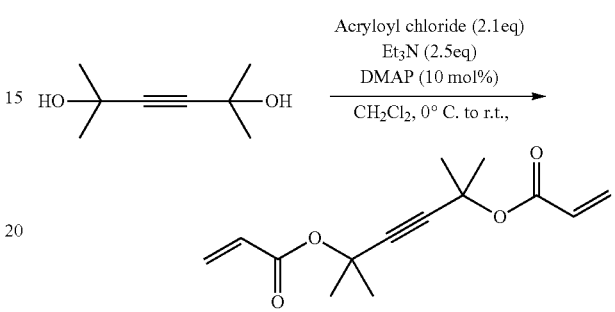

5.7 g of 2,5-dimethylhex-3-yne-2,5-diol synthesized in (1) was dissolved in CH$_2$Cl$_2$ (1.0 M) and the temperature was decreased to 0° C. while stirring. 12.6 g (2.5 equivalents) of triethylamine and 610 mg (0.1 equivalent) of DMAP were added, and then 9.5 g (2.1 equivalents) of acryloyl chloride was slowly added.

After completion of the addition, the reaction temperature was raised to room temperature and stirring was performed for about 12 hours. After completion of the reaction, the reaction solvent was filtered through a celite pad and the solvent was removed under vacuum. The remaining organic products were extracted with water and EA, and the remaining water in the organic layer was removed with Na$_2$SO$_4$. The solid phase was filtered off, and the remaining organic solvent was removed under vacuum to obtain the title crosslinking agent compound in a yield of 91%.

1H NMR (500 MHz, CDCl3): δ 6.34 (dd, J=17.4, 1.2 Hz, 2H), 6.06 (dd, J=17.5, 10.5 Hz, 2H), 5.77 (dd, J=10.5, 1.2 Hz, 2H), 1.67 (s, 12H)

Example 3

Synthesis of 1-(3-(acryloyloxy)-3-methylbut-1-yn-1-yl)cyclohexyl acrylate (1) Synthesis of Diol Compound

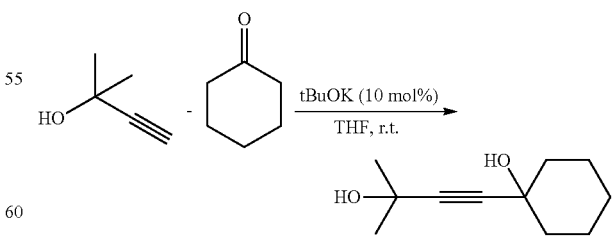

611 mg (0.1 equivalent) of tBuOK (potassium tert-butoxide) was dissolved in THF, and then cooled to 0° C. under stirring. To this reaction solution, 4.2 g of 2-methylbut-3-yn-2-ol (reference material, 1 equivalent) dissolved in THF was slowly added dropwise with paying attention to temperature rise. After stirring for about 30 minutes, 4.9 g (1 equivalent) of cyclohexanone was slowly added dropwise to the reaction solution. After completion of the injection, stirring was performed for about 12 hours while raising the reaction temperature to room temperature. After TLC was used to determine the completion of the reaction, the reaction mixture was decompressed to remove THF and unreacted acetone. Water and hexane were added to the remaining organic oil to remove nonpolar side reaction products with a hexane layer.

An aqueous layer was saturated by adding salt thereto, and extracted three to four times using EA. The resulting 1-(3-hydroxy-3-methylbut-1-yn-1-yl)cyclohexan-1-ol was extracted as an organic layer, and the remaining water in the organic layer was removed with $Na_2SO_4$. A solid phase was removed using a filter and the remaining organic solvent was removed under vacuum to obtain a desired 1-(3-hydroxy-3-methylbut-1-yn-1-yl)cyclohexan-1-ol in a yield of about 67%.

(2) Synthesis of Crosslinking Agent Compound

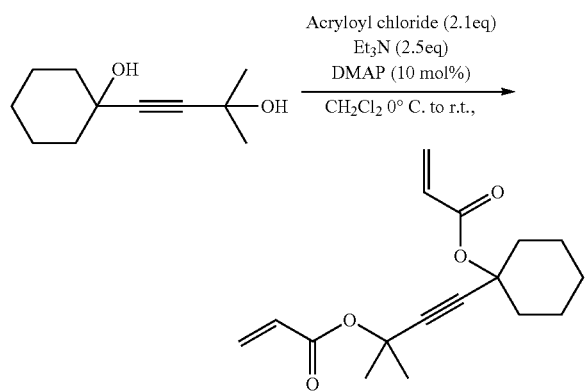

1.4 g of 1-(3-hydroxy-3-methylbut-1-yn-1-yl)cyclohexan-1-ol synthesized in (1) was dissolved in $CH_2Cl_2$ (1.0 M) and the temperature was decreased to 0° C. while stirring. 1.3 g (2.5 equivalents) of triethylamine and 61 mg (0.1 equivalent) of DMAP were added, and then 950 mg (2.1 equivalents) of acryloyl chloride was slowly added.

After completion of the addition, the reaction temperature was raised to room temperature and stirring was performed for about 12 hours. After completion of the reaction, the reaction solvent was filtered through a celite pad and the solvent was removed under vacuum. The remaining organic products were extracted with water and EA, and the remaining water in the organic layer was removed with $Na_2SO_4$. The solid phase was filtered off, and the remaining organic solvent was removed under vacuum to obtain the title crosslinking agent compound in a yield of 62%.

1H NMR (500 MHz, CDCl3): δ 6.37-6.32 (m, 2H), 6.10-6.03 (m, 2H), 5.80-5.76 (m, 2H), 1.80-1.50 (m, 10H), 1.70 (s, 6H)

Comparative Example 1

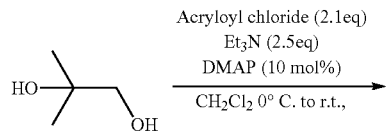

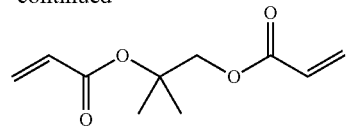

2.7 g (1 equivalent, reference material) of 2-methylpropane-1,2-diol was dissolved in $CH_2Cl_2$ (2.0 M), and the temperature was decreased to 0° C. while stirring. 7.6 g (2.5 equivalents) of TEA and 366 mg (0.1 equivalent) of DMAP were added, and then 5.7 g (2.1 equivalents) of acryloyl chloride was slowly added. After completion of the addition, the reaction temperature was raised to room temperature and stirring was performed for about 12 hours. After completion of the reaction, the reaction solvent was removed under vacuum. At this time, when $CH_2Cl_2$ was removed to some extent, it was confirmed that a solid was precipitated. This solid was dissolved in water, and extracted with EA three times, and the remaining water in the collected organic layer was removed with $Na_2SO_4$.

The organic solvent was removed under vacuum, and hexane was added to the resulting brown oil. The resulting solid phase was removed through a celite pad, and the resulting light yellow solution was concentrated under reduced pressure to obtain clear oil-phase 2-methylpropane-1,2-diyldiacrylate in a yield of 81%.

1H NMR (500 MHz, CDCl3): δ 6.42 (dd, J=17.2, 1.2 Hz, 1H), 6.31 (dd, J=17.3, 1.2 Hz, 1H), 6.17 (dd, J=17.4, 10.3 Hz, 1H), 6.06 (dd, J=17.5, 10.5 Hz, 1H), 5.86 (dd, J=10.2, 1.2 Hz, 1H), 5.76 (dd, J=10.5, 1.1 Hz, 1H), 4.36, (s, 2H), 1.54 (s, 6H)

<Preparation Example of Superabsorbent Polymer>

Example 4

To a glass reactor, 100 g of acrylic acid, 0.6 g of the crosslinking agent of Example 1 as an internal crosslinking agent, 0.008 g of Irgacure TPO (diphenyl(2,4,6-trimethylbenzoyl)phosphine oxide), 0.18 g of laponite, and 55 g of water were introduced. To the glass reactor, 123.5 g of 32 wt % caustic soda solution was slowly added dropwise and mixed.

When the caustic soda solution was added dropwise, the temperature of the mixed solution was increased by the heat of neutralization. Thus, the mixed solution was allowed to cool. When the temperature of the mixed solution was cooled to about 40° C., 0.2 g of sodium persulfate was added to the mixed solution to prepare a monomer mixture.

The monomer mixture was fed at a rate of 500 mL/min to 2000 mL/min on a conveyor belt with a width of 10 cm and a length of 2 m rotating at a speed of 50 cm/min. In addition, the polymerization reaction was performed for 60 seconds by irradiating ultraviolet rays with an intensity of 10 mW/cm$^2$ simultaneously with the supply of the monomer mixture.

In addition, the polymer obtained through the polymerization reaction was prepared as crumbs by passing through a hole having a diameter of 10 mm using a meat chopper. Subsequently, the crumbs were uniformly dried in an oven capable of shifting airflow up and down by flowing hot air at 185° C. from the bottom to the top for 20 minutes and from the top to the bottom for 20 minutes. The dried crumbs were pulverized using a pulverizer and size-sorted to obtain a base resin having a size of 150 μm to 850 μm.

To 100 g of the prepared base resin powder, a mixture of 3.2 g of ultra-pure water, 4.0 g of methanol, 0.088 g of ethylene carbonate, and 0.01 g of silica (product name: REOLOSIL DM30S, manufacturer: Tokuyama Corporation) was introduced and mixed for 1 minute, and surface crosslinking reaction was allowed at 185° C. for 90 minutes.

Then, the resulting product was pulverized and size-sorted to obtain a superabsorbent polymer having a particle size of 150 µm to 850 µm.

Example 5

A superabsorbent polymer was prepared in the same manner as in Example 4, except that 0.6 g of the crosslinking agent of Example 2 was used, instead of the crosslinking agent of Example 1, as the internal crosslinking agent.

Example 6

A superabsorbent polymer was prepared in the same manner as in Example 4, except that 0.6 g of the crosslinking agent of Example 3 was used, instead of the crosslinking agent of Example 1, as the internal crosslinking agent.

Comparative Example 2

A superabsorbent polymer was prepared in the same manner as in Example 1, except that 0.26 g of polyethylene glycol diacrylate (PEGDA) was used, instead of the crosslinking agent of Example 1, as the internal crosslinking agent.

Comparative Example 3

A superabsorbent polymer was prepared in the same manner as in Example 4, except that 0.6 g of the crosslinking agent of Comparative Example 1 was used, instead of the crosslinking agent of Example 1, as the internal cros slinking agent.

Experimental Example

Evaluation of Thermal Degradability of Base Resin

To evaluate thermal degradability at a high temperature and changes in absorbency with respect to the polymer obtained by polymerizing the crosslinking agent compound of the present invention and the acrylic acid-based monomer, the base resins (before surface crosslinking) of Examples and Comparative Examples were heat-treated at 185° C., and changes in centrifuge retention capacity over time were measured and described in Table 1 below.

(1) Centrifuge Retention Capacity (CRC)

Centrifuge retention capacity by absorbency under no load was measured for the superabsorbent polymer with respect to a saline solution in accordance with EDANA NWSP 241.0.R2.

In detail, among the superabsorbent polymers of which centrifuge retention capacity was to be measured, a sample with a particle diameter of 150 µm to 850 µm, which passed through a US standard 20 mesh screen, and remained on a US standard 100 mesh screen, was prepared.

Then, $W_0$ (g, about 0.2 g) of the sample having a particle diameter of 150 µm to 850 µm were uniformly put in a bag made of non-woven fabric, and the bag was sealed. Then, the bag was immersed in a 0.9 wt % sodium chloride aqueous solution (saline solution) at room temperature. After 30 minutes, the bag was drained at 250 G for 3 minutes using a centrifuge, and then the weight $W_2$(g) of the bag was measured. Meanwhile, after the same operation was performed using an empty bag without the sample, the weight $W_1$(g) at that time was measured.

By using the obtained weights, centrifuge retention capacity was calculated according to the following Equation 1.

$$CRC(g/g) = \{[W_2(g) - W_1(g)]/W_0(g)\} - 1 \quad \text{[Equation 1]}$$

In Equation 1, $W_0$(g) is the initial weight (g) of the sample having a particle diameter of 150 µm to 850 µm, $W_1$(g) is the weight of an empty bag made of nonwoven fabric, which was measured after the empty bag without the sample was immersed in a saline solution at room temperature for 30 minutes, and then drained using a centrifuge at 250 G for 3 minutes, and $W_2$(g) is the weight of a bag made of nonwoven fabric including the sample, which was measured after the bag made of nonwoven fabric including the sample was immersed in a saline solution at room temperature for 30 minutes, and then drained using a centrifuge at 250 G for 3 minutes.

TABLE 1

|  | Heat treatment time (min, 185° C.) | CRC (g/g) |
| --- | --- | --- |
| Example 4 | 0 | 33.6 |
|  | 20 | 35.6 |
|  | 40 | 36.7 |
|  | 60 | 37.3 |
| Example 5 | 0 | 47.8 |
|  | 20 | 54.0 |
|  | 40 | 58.7 |
|  | 60 | 58.9 |
| Example 6 | 0 | 49.2 |
|  | 20 | 50.7 |
|  | 40 | 52.8 |
|  | 60 | 53.4 |
| Comparative Example 2 | 0 | 50.2 |
|  | 20 | 51.9 |
|  | 40 | 50.6 |
| Comparative Example 3 | 0 | 31 |
|  | 20 | 33.4 |
|  | 40 | 35.7 |
|  | 60 | 38.4 |

Referring to Table 1, Examples 4 to 6, in which crosslinking polymerization of the acrylic acid monomer was performed in the presence of the novel crosslinking agent compound of Chemical Formula 1, showed increased centrifuge retention capacity over time, when heat-treated at a high temperature (185° C.). This may be because the internal crosslinked structure of the polymer was degraded by the high temperature, and as a result, the crosslinking density was lowered.

In contrast, Comparative Example 2, in which the existing crosslinking agent was used, showed no significant increase in the centrifuge retention capacity even after the heat treatment time passed. Comparative Example 3 had a tendency to have increased centrifuge retention capacity with the heat treatment time, but its initial centrifuge retention capacity was low.

Evaluation of Physical Properties of Superabsorbent Polymer

Physical properties were evaluated for the surface-crosslinked superabsorbent polymers of Examples 4, 5, and 6 and Comparative Examples 2 and 3 by the following methods.

(1) Centrifuge Retention Capacity (CRC)

Centrifuge retention capacity was measured in accordance with EDANA NWSP 241.0.R2. A detailed experimental method is the same as in the method of measuring the centrifuge retention capacity of the base resin.

(2) Absorbency Under Pressure (AUP)

Absorbency under pressure of 0.7 psi was measured for each superabsorbent polymer in accordance with EDANA NWSP 242.0.R2.

In detail, a 400 mesh screen made of stainless steel was installed on the bottom of a plastic cylinder with an inner diameter of 25 mm. Under the conditions of room temperature and relative humidity of 50%, $W_0(g)$ (0.9 g) of the superabsorbent polymer was uniformly scattered on the screen. Subsequently, a piston capable of uniformly providing a load of 0.7 psi was put thereon, in which the piston having an outer diameter slightly smaller than 25 mm was used such that there was no gap with the inner wall of the cylinder, and the movement upward and downward was not hindered. At this time, the weight $W_3(g)$ of the apparatus was measured.

On the inner side of a petri dish with a diameter of 150 mm, a glass filter with a diameter of 90 mm and a thickness of 5 mm was positioned, and a saline solution composed of 0.9 wt % sodium chloride was poured on the petri dish until the water level of the saline solution became horizontal to the upper side of the glass filter. One sheet of filter paper with a diameter of 90 mm was put thereon. The apparatus was mounted on the filter paper so that the superabsorbent polymer was allowed to absorb the liquid under load for 1 hour. After 1 hour, the apparatus was lift up and its weight $W_4(g)$ was measured.

By using the measured weights, absorbency under pressure (g/g) was calculated according to the following Equation.

$$AUP(g/g)=[W_4(g)-W_3(g)]/W_0(g) \quad [\text{Equation 2}]$$

TABLE 2

| | CRC (g/g) | AUP (g/g, 0.7 psi) |
|---|---|---|
| Example 4 | 34.0 | 25.7 |
| Example 5 | 42.5 | 22.6 |
| Example 6 | 37.8 | 23.5 |
| Comparative Example 2 | 36.9 | 23.7 |
| Comparative Example 3 | 32.4 | 24.8 |

Referring to Table 2, it was confirmed that when Example 4 and Comparative Example 2 or 3 having similar water retention capacity were compared with each other, the superabsorbent polymer according to Example of the present invention exhibited more improved absorbency under pressure. Further, Examples 5 and 6 exhibited higher water retention capacity than Comparative Examples, while maintaining absorbency under pressure equivalent thereto.

When Examples are compared with each other, Examples 4 and 5 were slightly better than Example 6 in terms of the effect of improving water retention capacity and absorbency under pressure at the same time.

The invention claimed is:

1. A composition comprising a crosslinking agent compound represented by Chemical Formula 1, and an acrylic acid-based monomer:

[Chemical Formula 1]

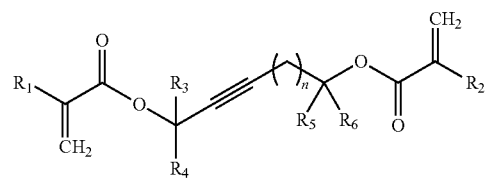

in Chemical Formula 1, $R_1$ and $R_2$ are each independently hydrogen or methyl, $R_3$ and $R_4$ are each independently alkyl having 1 to 20 carbon atoms, $R_5$ and $R_6$ are each independently hydrogen, alkyl having 1 to 20 carbon atoms, or cycloalkyl having 3 to 20 carbon atoms, or $R_5$ and $R_6$ are connected to each other to form a divalent aliphatic ring, and n is an integer of 0 to 10.

2. The composition of claim 1, wherein $R_1$ and $R_2$ are hydrogen.

3. The composition of claim 1, wherein $R_3$ and $R_4$ are each independently alkyl having 1 to 20 carbon atoms, and $R_5$ and $R_6$ are each independently hydrogen, alkyl having 1 to 5 carbon atoms, or divalent form of cycloalkane formed by connecting two or more groups adjacent to each other.

4. The composition of claim 3, wherein $R_3$ and $R_4$ are each independently methyl, or ethyl, and $R_5$ and $R_6$ are each independently hydrogen, methyl, or ethyl.

5. The composition of claim 1, wherein n is an integer of 0 to 5.

6. The composition crosslinking agent compound of claim 1, wherein Chemical Formula 1 is selected from compounds represented by the following Chemical Formulae 1-1 to 1-3:

[Chemical Formula 1-1]

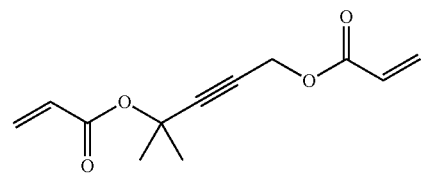

[Chemical Formula 1-2]

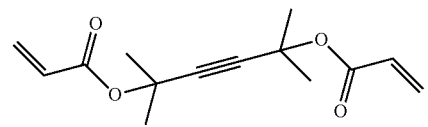

[Chemical Formula 1-3]

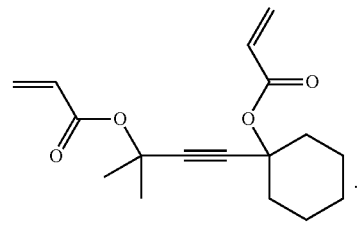

7. A superabsorbent polymer comprising a polymer which is obtained by polymerizing the composition of claim 1, wherein the polymer comprises a thermally degradable internal crosslinked structure.

8. The superabsorbent polymer of claim 7, wherein the acrylic acid-based monomer is represented by the following Chemical Formula 2:

R-COOM  [Chemical Formula 2]

in Chemical Formula 1,

R is an alkyl group containing an unsaturated bond and having 2 to 5 carbon atoms, and M is a hydrogen atom, a monovalent or divalent metal, an ammonium group, or an organic amine salt.

9. The superabsorbent polymer of claim 7, wherein the polymer is configured to be thermally degraded at a temperature of 180° C. or higher.

10. The superabsorbent polymer of claim 7, further comprising a surface-crosslinked layer which is formed on the surface of the polymer.

11. The superabsorbent polymer of claim 7, wherein the polymer has 5% to 30% increased centrifuge retention capacity (CRC) after exposure to a temperature of 185° C. for 40 minutes as compared with that before the exposure to the temperature of 185° C. for 40 minutes.

12. The superabsorbent polymer of claim 10, wherein the surface-crosslinked layer is formed on the surface of the polymer by performing a surface crosslinking reaction at a temperature of 180° C. or higher.

13. The superabsorbent polymer of claim 10, wherein the superabsorbent polymer has centrifuge retention capacity (CRC) from 33 g/g to 50 g/g and absorbency under pressure (AUP) of 0.7 psi of 21 g/g to 30 g/g.

* * * * *